(12) United States Patent
Kutzki et al.

(10) Patent No.: US 8,344,182 B2
(45) Date of Patent: Jan. 1, 2013

(54) PROCESS FOR THE PREPARATION OF (S)-2-AMINO-1-PROPANOL (L-ALANINOL) FROM (S)-1-METHOXY-2-PROPYLAMINE

(75) Inventors: Olaf Kutzki, Mannheim (DE); Klaus Ditrich, Goennheim (DE); Michael Bartsch, Hirzel (CH)

(73) Assignee: BASF SE, Ludwigshafen (DE)

( * ) Notice: Subject to any disclaimer, the term of this patent is extended or adjusted under 35 U.S.C. 154(b) by 324 days.

(21) Appl. No.: 12/745,836

(22) PCT Filed: Dec. 10, 2008

(86) PCT No.: PCT/EP2008/067181
§ 371 (c)(1),
(2), (4) Date: Jun. 2, 2010

(87) PCT Pub. No.: WO2009/080505
PCT Pub. Date: Jul. 2, 2009

(65) Prior Publication Data
US 2010/0240928 A1    Sep. 23, 2010

(30) Foreign Application Priority Data
Dec. 20, 2007    (EP) .................................... 07150226

(51) Int. Cl.
*C07C 213/00* (2006.01)
*C07C 215/08* (2006.01)
(52) U.S. Cl. ...................................................... 564/503
(58) Field of Classification Search .................... 568/907
See application file for complete search history.

(56) References Cited

U.S. PATENT DOCUMENTS
2007/0135648 A1    6/2007    Urtel et al.

FOREIGN PATENT DOCUMENTS
| JP | 06199747 | 12/1992 |
|---|---|---|
| WO | 99 07199 | 2/1999 |
| WO | 01 73038 | 10/2001 |
| WO | 2005 077871 | 8/2005 |

OTHER PUBLICATIONS

Kurihara, Yoshie et al., "The Addition Reaction of Dinitrogen Trioxide with Cinnamyl Acetate", Bulletin of the Chemical Society of Japan, vol. 38, No. 8, pp. 1327-1330, CODEN: BCSJA8, ISSN: 0009-2673, XP002515489, (Aug. 1965).
Schreyer, R. C. et al., "Synthesis of 3-Amino-1,2-propanediol and 2,3-Diamino-1-propanol", Journal of the American Chemical Society, vol. 73, pp. 4404-4405, CODEN: JACSAT; ISSN: 0002-7863, XP008102394, (Sep. 1951).
Karrer, P. et al., $\Delta^{3,5}$-Cholestadien-7-on aus Rindsleber. (Vorlaeufige Mitteilung), Helvetica Chimica ACTA, vol. 31, pp. 1617-1623, (1948).
Jeger, O. et al., "Eine Methode zur Ueberfuehrung von Carbonsaeuren in primaere Alkohole", Helvetica Chimica ACTA, vol. 29, No. 48, pp. 684-692, (1946).
Ghorai, K. Manas et al., "A convenient synthetic route to enantiopure N-tosylazetidines from α-amino acids", Tetrahedron Letters, vol. 48, pp. 2471-2475, (2007).
Schoen, Istvan et al., "Sodium-Liquid Ammonia Reduction of Carboxamides to Alcohols", J. Org. Chem., vol. 48, No. 11, pp. 1916-1919, (1983).
Studer, Martin et al., "Catalytic Hydrogenation of Chiral α- Amino and α-Hydroxy Esters at Room Temperature with Nishimura Catalyst without Racemization", Adv. Synth. Catal. vol. 343, No. 8, pp. 802-808, (2001).

*Primary Examiner* — Brian J Davis
(74) *Attorney, Agent, or Firm* — Oblon, Spivak, McClelland, Maier & Neustadt, L.L.P.

(57) ABSTRACT

The invention relates to a process for the preparation of (S)-2-amino-1-propanol (L-alaninol) from (S)-1-methoxy-2-propylamine via the hydrochloride of (S)-2-amino-1-propanol and subsequent work-up.

20 Claims, No Drawings

PROCESS FOR THE PREPARATION OF (S)-2-AMINO-1-PROPANOL (L-ALANINOL) FROM (S)-1-METHOXY-2-PROPYLAMINE

The invention relates to a process for the preparation of (S)-2-amino-1-propanol (L-alaninol) from (S)-1-methoxy-2-propylamine via the hydrochloride of (S)-2-amino-1-propanol and subsequent work-up.

There is a great need for (S)-2-amino-1-propanol, which is of great importance as an intermediate for pharmaceutical active ingredients such as, for example, the antibiotic Levofloxacin.

(S)-2-Amino-1-propanol is already known and can be prepared by various processes. Starting materials for the first processes for the preparation of (S)-2-amino-1-propanol have been derivatives of the amino acid L-alanine. For example, Karrer et al. described in Helv. Chim. Acta 1948, 31, 1617 and in JP-A 6199747 the reduction of the corresponding esters of the amino acid L-alanine to (S)-2-amino-1-propanol.

Further reductions have been described starting from the thio esters of L-alanine by Jeger et al. in Helv. Chim. Acta 1946 29, 684. The reduction of the corresponding L-alanine is described by M. K. Ghorai et al. in Tetrahedron Lett. 2007, 48, 2471, and also in WO 2005/077871. The reduction of amide derivatives of L-alanine has also already been disclosed by I. Schön et al. in J. Org. Chem. 1983, 48, 1916. M. Studer et al. describe in Adv. Synth. Catal. 2001, 343, 802 the catalytic hydrogenation of an alanine ester to give (S)-2-amino-1-propanol.

As a further option for producing (S)-2-amino-1-propanol, WO-A2 99/07199 and WO-A2 01/73038 describe the enzymatic conversion of 2-aminopropane to (S)-2-amino-1-propanol.

The cleavage of methyl ethers through the use of hydrochloric acid is described both at atmospheric pressure by Schreyer et al. in J. Am. Chem. Soc. 1951, 73, 4404, and also under increased pressure by Kurihara et al. in Bull. Chem. Soc. Jpn. 1965, 38, 1327.

Disadvantages of all of these described processes are firstly the use of metal hydrides for the reductions of the individual amino acid derivatives since these are very expensive and are also difficult to remove from the subsequently produced product and secondly, in the case of enzymatic processes, the very long reaction times, the low yields and also the large dilutions in which it is necessary to work. A disadvantage of the catalytic hydrogenation of ester derivatives of alanine is the large amount of catalyst required.

It is therefore the object of the present invention to provide a process which is as cost-effective as possible compared with the prior art hitherto but which nevertheless allows (S)-2-amino-1-propanol to be obtained with similarly high ee values and in similarly good yields as described in the prior art.

This object is achieved by a process for the preparation of (S)-2-amino-1-propanol comprising the following steps:

I) reaction of (S)-1-methoxy-2-propylamine with at least 2 equivalents of a 30 to 40% strength by weight hydrochloric acid, either
  Ia) at temperatures greater than 80° C. in an autoclave at pressures in the range from 3 to 45 bar for 1 to 12 hours and subsequent cooling to room temperature and decompression of the autoclave or
  Ib) it is heated at reflux for 30 to 60 hours at atmospheric pressure,
II) then the aqueous solvent is distilled off from step Ia) or from step Ib)
III) then the reaction product from step II) is either
  IIIa) admixed with an inorganic base until a pH greater than 10 has been established or
  IIIb) the product obtained from step II is reacted with a mixture of a relatively high-boiling solvent and a relatively strong base,
IV) then either
  IVa) the reaction product from step IIIa is freed from the water by distillation and the residue is admixed with a solvent and then filtered, or
  IVb) the reaction product from step IIIa is admixed with a mixture of an azeotrope-forming organic solvent and a relatively high-boiling diluent, and water and (S)-2-aminopropan-1-ol are distilled off azeotropically together with the azeotrope-forming organic solvent, then the (S)-2-aminopropan-1-ol-comprising distillation fractions are combined,
V) the filtrate obtained from step IVa) or the combined filtrates obtained from step IVb) or the mixtures obtained from step IIIb) are distilled.

The process according to the invention is advantageous when a 35 to 38% strength hydrochloric acid is used in step I.

The process according to the invention is advantageous when, at a temperature in the range from 80 to 100° C., the reaction in step Ia) lasts more than 9 hours and the pressure is between 3 and 5 bar.

The process according to the invention is advantageous when, at a temperature in the range of more than 100° C., the reaction in step Ia) lasts less than 9 hours and the pressure is between 15 and 45 bar.

The process according to the invention is advantageous when, at a temperature in the range from 130 to 135° C., the reaction in step Ia) lasts less than 4.5 hours and the pressure is between 19-30 bar.

The process according to the invention is advantageous when, according to step Ib), heating is carried out at reflux for 45-60 hours.

The process according to the invention is advantageous when, according to step Ib), after 15 hours, a further 1-2 equivalents of a 30 to 40% strength by weight hydrochloric acid are added and heating is carried out at reflux for a total of 30-50 hours.

The process according to the invention is advantageous when the inorganic base used in step IIIa) is selected from the group of sodium hydroxide, potassium hydroxide, lithium hydroxide, calcium hydroxide, sodium carbonate, potassium carbonate, potassium hydrogencarbonate or sodium hydrogencarbonate.

The process according to the invention is advantageous when the pH in step IIIa is greater than or equal to 12.

The process according to the invention is advantageous when the relatively high-boiling solvent used in step IIIb is selected from the group of glycols having 2 to 8 carbon atoms, such as ethylene glycol, diethylene glycol and triethylene glycol, or polyalkylene glycols, such as e.g. products of the brands Pluriol E and P® (alkoxylates of ethylene oxide or propylene oxide from BASF AG), in particular Pluriol® P600 (polypropylene oxide from BASF AG, kinematic viscosity ca. 130 mm$^2$/s at 20° C.), or products of the brand Lutron® (modified polyglycol ethers from BASF AG), in particular Lutron® HF1 (modified polyglycol ether from BASF AG, kinematic viscosity 220-280 mm$^2$/s at 23° C.), or amino alcohols, such as ethanolamine, diethanolamine and triethanolamine, or mixtures of these solvents, and also mixtures thereof with water.

The process according to the invention is advantageous when the relatively strong base used in step IIIb is selected from the group of alkali metal hydroxides such as sodium hydroxide, potassium hydroxide, or alkaline earth metal hydroxides such as calcium hydroxide, or alkali metal alcoholates, such as sodium methanolate, sodium ethanolate, potassium ethanolate, sodium tert-butanolate and potassium tert-butanolate or diazabicyclooctane (DABCO), diazabicyclononane (DBN), diazabicyclo-undecane (DBU) and tri-n-octylamine.

The process according to the invention is advantageous when the solvent which is used in step IVa) is selected from the group of methanol, ethanol, n-propanol, isopropanol, n-butanol, 2-butanol (sec-butanol), 2-methyl-1-propanol (isobutanol), ethyl acetate, methyl acetate or dichloromethane. Very particular preference is given to methanol.

The process according to the invention is advantageous when the azeotrope-forming organic solvent in step IVb) is selected from the group of toluene, o-, m- and p-xylene, and also ethylbenzene and mixtures thereof, preference being given to o-, m- and p-xylene and technical-grade mixtures thereof which can comprise up to 25% by weight of ethylbenzene.

The process according to the invention is advantageous when the distillation in step V is carried out at a pressure of from 2 to 6 mbar.

For the process according to the invention, (S)-1-methoxy-2-propylamine is reacted with hydrochloric acid to give (S)-2-amino-1-propanol hydrochloride, and then, by means of appropriate work-up, (S)-2-amino-1-propanol is liberated according to the following reaction:

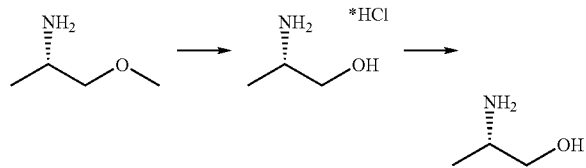

For the formation of the (S)-2-amino-1-propanol hydrochloride, (S)-1-methoxy-2-propylamine is reacted with at least 2 equivalents of a 30 to 40% strength by weight hydrochloric acid solution, particularly preferably a 35 to 38% strength by weight hydrochloric acid solution, very particularly preferably a 37% strength by weight hydrochloric acid solution. Preference is given to the addition of from 2 to 5 equivalents of 30 to 40% strength by weight hydrochloric acid.

The reaction with the hydrochloric acid can take place in two different ways, although both lead to the hydrochloride of (S)-2-amino-1-propanol.

In the one variant, following the complete addition of the hydrochloric acid, the mixture obtained is placed in an autoclave. Stirring is then carried out at temperatures greater than 80° C., preferably ≧90° C., very particularly preferably in the range from 135 to 140° C., and at pressures of from 3 to 45 bar, preferably 19 to 30 bar, for 1 to 12 hours, preferably ≦10 hours, very preferably ≦4 hours. After the reaction has taken place in the autoclave, the autoclave is cooled to room temperature and then decompressed.

In the other reaction procedure, following the addition of the (S)-1-methoxy-2-propylamine to the hydrochloric acid, the resulting mixture is then heated at reflux for 30 to 60 hours, preferably 45 to 50 hours, where, at time intervals of 10-20 hours, in each case a further 0-2 equivalents of a 30 to 40% strength by weight hydrochloric acid are added.

For the preparation of the (S)-2-amino-1-propanol hydrochloride, the reaction in the autoclave is preferred over heating under reflux.

The product obtained following the reaction in the autoclave or the product obtained after heating under reflux is then freed from the water by distillation.

The hydrochloride of (S)-2-amino-1-propanol prepared in this way is then cooled at temperatures of less than 60° C., preferably in the range from 10 to 40° C. An aqueous solution of an inorganic base is then added dropwise with stirring to this chilled solution until the solution has a pH greater than 10, preferably greater than 12, very particularly preferably greater than 14. The inorganic bases here are selected from the group of sodium hydroxide, potassium hydroxide, lithium hydroxide, calcium hydroxide, sodium carbonate, potassium carbonate, potassium hydrogencarbonate or sodium hydrogencarbonate. Particular preference is given to using sodium hydroxide or potassium hydroxide. The inorganic base is preferably used as aqueous solution in concentrations between 10 and 50% by weight.

The solution prepared in this way can then be worked-up in various ways. In one variant, the water is distilled off under reduced pressure. This leaves a residue which is taken up in a solvent. The solvent here is selected from the group of methanol, ethanol, n-propanol, isopropanol, n-butanol, 2-butanol (sec-butanol), 2-methyl-1-propanol (isobutanol), dichloromethane, methyl acetate, ethyl acetate. This solution is then filtered.

In another variant of the work-up, the aqueous alkaline solution from step IIIa is admixed with a mixture of an azeotrope-forming organic solvent and a relatively high-boiling diluent. The azeotrope-forming organic solvent here is selected from the group of toluene, o-, m- and p-xylene, and also ethylbenzene and mixtures thereof, preference being given to o-, m- and p-xylene and technical-grade mixtures thereof which can comprise up to 25% by weight of ethylbenzene.

Relatively high-boiling diluent is to be understood as meaning diluents with a boiling point greater than 190° C. (at 1013 mbar) and also mixtures of the corresponding diluents, and mixtures thereof with water. The relatively high-boiling diluent here is selected from the group of polyalkylene glycols, such as e.g. products of the brands Pluriol E and P® (alkoxylates of ethylene oxide or propylene oxide from BASF AG), in particular Pluriol® P600 (polypropylene oxide from BASF AG, kinematic viscosity ca. 130 mm$^2$/s at 20° C.), or products of the brand Lutron® (modified polyglycol ethers from BASF AG), in particular Lutron® HF1 (modified polyglycol ether from BASF AG, kinematic viscosity 220-280 mm$^2$/s at 23° C.), or from the group of silicone oils, such as e.g. products of the brand Baysilone® M (polydimethylsiloxanes from Momentive Performance Materials), in particular Baysilone® M200 (polydimethylsiloxanes from Momentive Performance Materials, kinematic viscosity 200 mm$^2$/s at 20° C.), or paraffin oils. The mixing ratio of azeotrope-forming organic solvent to relatively high-boiling diluent is preferably in the range from 1:1 to 1:6, particularly preferably in the range from 1:1.

Then, from this mixture, water, (S)-2-amino-1-propanol and an azeotropic mixture of these two compounds are distilled off together with the azeotrope-forming organic solvent. The (S)-2-amino-1-propanol-comprising fractions are then combined again.

Then, either the filtrate from reaction step IVa) or the (S)-2-amino-1-propanol-comprising fractions from step IVb) is/are distilled.

As an alternative work-up, the product obtained from step II can also be reacted with a mixture of a relatively high-boiling solvent and a relatively strong base, where the free (S)-2-amino-1-propanol is then removed by means of distillation. Solvents with a boiling point greater than 190° C. (at 1013 mbar) can be used as relatively high-boiling solvent. Preferred relatively high-boiling solvents are glycols having 2 to 8 carbon atoms, such as ethylene glycol, diethylene glycol and triethylene glycol, or polyalkylene glycols, such as e.g. products of the brands Pluriol E and P® (alkoxylates of ethylene oxide or propylene oxide from BASF AG), in particular Pluriol® P600 (polypropylene oxide from BASF AG, kinematic viscosity ca. 130 mm²/s at 20° C.), or products of the brand Lutron® (modified polyglycol ethers from BASF AG), in particular Lutron® HF1 (modified polyglycol ether from BASF AG, kinematic viscosity 220-280 mm²/s at 23° C.), or amino alcohols, such as ethanolamine, diethanolamine and triethanolamine or mixtures of these solvents, and mixtures thereof with water.

Relatively strong bases are to be understood as meaning those which are selected from the group of alkali metal hydroxides, such as sodium hydroxide, potassium hydroxide or alkaline earth metal hydroxides, such as calcium hydroxide, or alkali metal alcoholates, such as sodium methanolate, sodium ethanolate, potassium ethanolate, sodium tert-butanolate and potassium tert-butanolate or diazabicyclooctane (DABCO), diazabicyclononane (DBN), diazabicycloundecane (DBU) and tri-n-octylamine.

The (S)-2-amino-1-propanol prepared by the process according to the invention has an ee value which corresponds to the ee value of the (S)-1-methoxy-2-propylamine used and can be obtained in yields of >50%.

EXAMPLES

Reaction Procedure 1 (According to the Invention)

(S)-1-Methoxy-2-propylamine (53.5 g, 0.6 mol, ee >99%) is added to 148 g (1.5 mol) of 37% strength by weight aqueous hydrochloric acid, the addition being carried out so slowly that the temperature remains below 30° C. The reaction mixture is then stirred for 4 hours at a temperature of 135° C. in an autoclave rendered inert with nitrogen at an autogenous pressure of 19-30 bar. After the reaction, the mixture is cooled to room temperature and carefully decompressed. Distilling off the water gives a very viscous oil-like liquid of (S)-2-amino-propan-1-ol hydrochloride (complete conversion according to NMR and GC).

Reaction Procedure 2 (According to the Invention)

(S)-1-Methoxy-2-propylamine (53.5 g, 0.6 mol, ee >99%) is added to 148 g (1.5 mol) of 37% strength by weight aqueous hydrochloric acid, the addition being carried out so slowly that the temperature is kept below 30° C. The reaction mixture is then stirred for 10 hours at a temperature of 90° C. in an autoclave rendered inert with nitrogen at a maximum of 5 bar (the pressure is always decompressed to 3 bar upon reaching 5 bar). After the reaction, the mixture is cooled to room temperature and carefully decompressed. Distilling off the water gives a very viscous oil-like liquid of (S)-2-aminopropan-1-ol hydrochloride (complete conversion according to NMR and GC).

Reaction Procedure 3 (According to the Invention)

(S)-1-Methoxy-2-propylamine (53.5 g, 0.6 mol, ee >99%) is slowly added to 148 g (1.5 mol) of 37% strength by weight aqueous hydrochloric acid, during which the temperature is kept below 30° C. The reaction mixture is then boiled under reflux (temperature: 100° C.) for 48 hours. The mixture is then cooled to room temperature. Distilling off the water gives a very viscous oil-like liquid of (S)-2-aminopropan-1-ol hydrochloride (complete conversion according to NMR and GC).

Reaction Procedure 4 (According to the Invention)

(S)-1-Methoxy-2-propylamine (53.5 g, 0.6 mol, ee >99%) is slowly added to 148 g (1.5 mol) of 37% strength by weight aqueous hydrochloric acid, during which the temperature is kept below 30° C. The reaction mixture is then boiled under reflux (temperature: 100° C.) for 15 hours before being admixed with a further 70 g (0.71 mol) of 37% strength by weight aqueous hydrochloric acid and boiled under reflux (temperature: 100° C.) for a further 20 hours. The mixture is then cooled to room temperature. Distilling off the water gives a very viscous oil-like liquid of (S)-2-aminopropan-1-ol hydrochloride (complete conversion according to GC).

Analytics ((S)-2-aminopropan-1-ol hydrochloride):
$^1$H-NMR (MeOD, 500 MHz): δ=1.35 (d, 3H), 3.41 (m, 1H), 3.60 (m, 1H), 3.77 (m, 1H).
$^{13}$C-NMR (MeOD, 125 MHz): δ=15 (s), 51 (m), 64 (s).

Experimental Examples

| No. | Reaction time [h] | Temperature [° C.] | Pressure [bar] | Conversion [GC area %] | Yield [GC area %] | Reaction procedure |
|---|---|---|---|---|---|---|
| 1 | 2 | 135 | 19 | 100 | 88.1 | 1 |
| 2 | 2 | 135 | 23 | 100 | 77.7 | 1 |
| 3 | 2 | 135 | 42 | 91.6 | 91.6 | 1 |
| 4 | 2 | 135 | 30 | 100 | 100 | 1 |
| 5 | 2 | 135 | 28 | 99.5 | 99.5 | 1 |
| 6 | 4 | 135 | 28 | 100 | 99.3 | 1 |
| 7 | 4 | 90 | 18 | 99.1 | 98.3 | 1 |
| 8 | 10 | 90 | 5 | 100 | 100 | 2 |
| 9 | 48 | 100 | 1 | 100 | 90 | 3 |
| 10 | 35 | 100 | 1 | 100 | 90 | 4 |

Liberating the free amine from the hydrochloride:

Work-Up 1 (According to the Invention)

(S)-2-Aminopropan-1-ol hydrochloride (from reaction procedure 1, 2, 3 or 4) is admixed with 100 ml of water (pH=0.76). With stirring and cooling, ca. 30 ml of 50% strength by weight aqueous NaOH solution is used to adjust the pH to ca. 12. The slurry-like residue that remains after distilling off (5 mbar) the water (NaCl precipitates out) is admixed with 100 ml of methanol and filtered. The filtrate is then freed from the methanol by distillation, giving 26.4 g (0.35 mol) of (S)-2-aminopropan-1-ol (confirmed by means of NMR+GC) (ee >99%).

Work-Up 2 (According to the Invention)

(S)-2-Aminopropan-1-ol hydrochloride (from reaction procedure 1, 2, 3 or 4) is admixed with 50 ml of water. With stirring and cooling, ca. 25 ml of 50% strength by weight aqueous NaOH solution is used to adjust the pH to ca. 14. After adding 50 g of Lutron® HF1 (modified polyglycol ether from BASF AG, kinematic viscosity 220-280 mm²/s at 23° C.) and 50 ml of xylene, the (S)-2-aminopropan-1-ol is distilled off in the mixture with water/xylene. The product-comprising fractions are combined and distillative removal (5 mbar) of the water/xylene gives 22.89 g (0.30 mol) of (S)-2-aminopropan-1-ol (confirmed by means of NMR+GC) (ee >99%).

Work-Up 3 (According to the Invention)

(S)-2-Aminopropan-1-ol hydrochloride (from reaction procedure 1, 2, 3 or 4) is admixed with 50 g of Pluriol® P600 (polypropylene oxide from BASF AG, kinematic viscosity ca. 130 mm$^2$/s at 20° C.). With stirring, the mixture is admixed with 0.6 mol (1 equivalent) of sodium methylate (30% by weight in methanol) and distilled (2 mbar). This gives 24.04 g (0.32 mol) of (S)-2-aminopropan-1-ol (confirmed by means of GC).

Analytics (free base):
$^1$H-NMR (MeOD, 500 MHz): δ=1.02 (d, 3H), 2.90 (m, 1H), 3.26 (m, 1H), 3.45 (m, 1H).
$^{13}$C-NMR (MeOD, 125 MHz): δ=19 (s), 49 (m), 69 (s).

The invention claimed is:

1. A process for the preparing (S)-2-amino-1-propanol comprising:
   1) reacting (S)-1-methoxy-2-propylamine with at least 2 equivalents of a 30 to 40% strength by weight hydrochloric acid, either
      Ia) at a temperature greater than 80° C. in an autoclave at a pressure of 3 to 45 bar for 1 to 12 hours and subsequently cooling to room temperature and decompressing of the autoclave
      or
      Ib) at reflux for 30 to 60 hours at atmospheric pressure;
   2) distilling off aqueous solvent to provide a first intermediate product;
   3) then either
      IIIa) admixing the first intermediate product with an inorganic base to a pH greater than 10, to provide a second intermediate product,
      or
      IIIb) reacting the first intermediate product with a mixture of a relatively high-boiling solvent and a relatively strong base;
   4) then either
      IVa) freeing the second intermediate product of IIIa) from water by distillation to provide a residue, admixing the residue with a solvent, and then filtering to give a filtrate,
      or
      IVb) mixing the second intermediate product of IIIa) with a mixture of an azeotrope-forming organic solvent and a relatively high-boiling diluent, to form an azeotropic mixture and azeotropically distilling off water and (S)-2-aminopropan-1-ol together with the azeotrope-forming organic solvent to separate at least one (S)-2-aminopropan-1-ol comprising distillation fraction from the azeotropic mixture, then, if the at least one (S)-2-aminopropan-1-ol-comprising distillation fraction comprises two or more distillation fractions, combining the two or more distillation fractions together to give a combined distillate;
   5) distilling the filtrate obtained from IVa), a (S)-2-aminopropan-1-ol-comprising distillation fraction or the combined distillate obtained from IVb), or the mixture obtained from IIIb).

2. The process according to claim 1, wherein the hydrochloric acid of 1) has a strength of 35 to 38%.

3. The process according to claim 1, comprising reacting 1) the (S)-1-methoxy-2-propylamine with the hydrochloric acid at a temperature Ia) of from greater than 80 to 100° C. in the autoclave at a pressure between 3 and 5 bar, such that the reacting 1) lasts more than 9 hours and up to 12 hours.

4. The process according to claim 1, comprising reacting 1) the (S)-1-methoxy-2-propylamine with the hydrochloric acid at a temperature Ia) of more than 100° C. in the autoclave at a pressure between 15 and 45 bar, such that the reacting 1) lasts for 1 hour to less than 9 hours.

5. The process according to claim 1, comprising reacting 1) the (S)-1-methoxy-2-propylamine with the hydrochloric acid at a temperature Ia) of 130 to 135° C. in the autoclave at a pressure between 19 and 30 bar, such that the reacting 1) lasts for 1 hour to less than 4.5 hours.

6. The process according to claim 1, comprising reacting 1) the (S)-1-methoxy-2-propylamine with the hydrochloric acid at a reflux Ib), such that the reacting 1) lasts for 45-60 hours.

7. The process according to claim 1, comprising reacting 1) the (S)-1-methoxy-2-propylamine with the hydrochloric acid at a reflux Ib), wherein, after 15 hours of the reflux Ib), a further 1-2 equivalents of a 30 to 40% strength by weight hydrochloric acid is added and the reflux Ib) is carried out for a total of 30-50 hours.

8. The process according to claim 1, comprising admixing IIIa) the first intermediate product with an inorganic base selected from the group consisting of sodium hydroxide, potassium hydroxide, lithium hydroxide, calcium hydroxide, sodium carbonate, potassium carbonate, potassium hydrogencarbonate, and sodium hydrogencarbonate.

9. The process according to claim 1, comprising admixing IIIa) the first intermediate product with an inorganic base to a pH of greater than or equal to 12.

10. The process according to claim 1, comprising reacting IIIb) the first intermediate product with a mixture of a relatively high-boiling solvent which is at least one selected from the group consisting of a glycol having 2 to 8 carbon atoms, a polyalkylene glycol, an amino alcohol, and water.

11. The process according to claim 1, comprising reacting IIIb) the first intermediate product with a mixture of a relative high-boiling solvent and a relatively strong base which is at least one selected from the group consisting of an alkali metal hydroxide, an alkaline earth metal hydroxide, an alkali metal alcoholate, diazabicyclooctane (DABCO), diazabicyclononane (DBN), diazabicycloundecane (DBU), and tri-n-octylamine.

12. The process according to claim 1, comprising freeing IVa) the second intermediate product of IIIa) from water by distillation to provide a residue, admixing the residue with a solvent selected from the group consisting of methanol, ethanol, n-propanol, isopropanol, n-butanol, 2-butanol, 2-methyl-1-propanol, dichloromethane, methyl acetate, and ethyl acetate, and then filtering to give a filtrate.

13. The process according to claim 1, comprising mixing IVb) the second intermediate product of IIIa) with a mixture of an azeotrope-forming organic solvent which is at least one selected from the group consisting of toluene, o-, m- and p-xylene, and ethylbenzene.

14. The process according to claim 1, wherein the distilling 5) is carried out at a pressure of from 2 to 6 mbar.

15. The process of claim 1, comprising reacting (S)-1-methoxy-2-propylamine with at least 2 equivalents of a 30 to 40% strength by weight hydrochloric acid at a temperature Ia) greater than 80° C. in an autoclave at a pressure of 3 to 45 bar for 1 to 12 hours and subsequently cooling to room temperature and decompressing of the autoclave.

16. The process of claim 1, comprising reacting (S)-1-methoxy-2-propylamine with at least 2 equivalents of a 30 to 40% strength by weight hydrochloric acid at reflux Ib) for 30 to 60 hours at atmospheric pressure.

17. The process of claim 1, comprising admixing IIIa) the first intermediate product with an inorganic base to a pH greater than 10, to provide a second intermediate product.

18. The process of claim 1, comprising reacting IIIb) the first intermediate product with a mixture of a relatively high-boiling solvent and a relatively strong base.

19. The process of claim 1, comprising:
admixing IIIa) the first intermediate product with an inorganic base to a pH greater than 10, to provide a second intermediate product; and
freeing IVa) the second intermediate product of IIIa) from water by distillation to provide a residue, admixing the residue with a solvent, and then filtering to give a filtrate.

20. The process of claim 1, comprising:
admixing IIIa) the first intermediate product with an inorganic base to a pH greater than 10, to provide a second intermediate product; and
mixing IVb) the second intermediate product of IIIa) with a mixture of an azeotrope-forming organic solvent and a relatively high-boiling diluent to form an azeotropic mixture, and azeotropically distilling off water and (S)-2-aminopropan-1-ol together with the azeotrope-forming organic solvent to separate at least one (S)-2-aminopropan-1-ol-comprising distillation fraction from the azeotropic mixture, then, if the at least one (S)-2-aminopropan-1-ol-comprising distillation fraction comprises two or more distillation fractions, combining the two or more distillation fractions together to give a combined distillate.

* * * * *